(12) United States Patent
Wolf et al.

(10) Patent No.: US 8,759,601 B2
(45) Date of Patent: Jun. 24, 2014

(54) METHOD FOR BIOGAS TREATMENT AND BIOGAS INSTALLATION

(75) Inventors: Markus Wolf, Neunberg vorm Wald (DE); Ulrich Nettelnbreker, Heek (DE)

(73) Assignee: Schmack Biogas AG (DE)

( * ) Notice: Subject to any disclaimer, the term of this patent is extended or adjusted under 35 U.S.C. 154(b) by 304 days.

(21) Appl. No.: 13/063,645

(22) PCT Filed: Aug. 24, 2009

(86) PCT No.: PCT/DE2009/075044
§ 371 (c)(1),
(2), (4) Date: May 2, 2011

(87) PCT Pub. No.: WO2010/028643
PCT Pub. Date: Mar. 18, 2010

(65) Prior Publication Data
US 2011/0245572 A1    Oct. 6, 2011

(30) Foreign Application Priority Data

Sep. 11, 2008 (DE) .......................... 10 2008 046 879

(51) Int. Cl.
*B01D 53/02* (2006.01)
*C07C 7/12* (2006.01)

(52) U.S. Cl.
USPC ............ 585/802; 585/818; 585/820; 95/139; 95/140

(58) Field of Classification Search
None
See application file for complete search history.

(56) References Cited

U.S. PATENT DOCUMENTS 4,780,415 A    10/1988    Ducellier et al.

FOREIGN PATENT DOCUMENTS

| AT | 410273 | 3/2003 |
|----|--------|--------|
| DE | 3782318 | 4/1993 |
| DE | 19947339 | 4/2001 |
| DE | 10047264 | 4/2002 |
| EP | 1301583 | 4/2003 |
| EP | 1681274 | 7/2006 |
| EP | 1811011 | 7/2007 |
| JP | 1979-76001 | 1/1981 |
| JP | 57105296 | 6/1982 |

OTHER PUBLICATIONS

International Search Report for International Patent Application No PCT/DE2009/075044 dated May 26, 2010.

*Primary Examiner* — Tam M Nguyen
(74) *Attorney, Agent, or Firm* — Daniel A. Thomson; Emerson Thomson Bennett, LLC

(57) ABSTRACT

The invention relates to a method for biogas treatment, wherein the gas originating from a fermentation is separated into a usable biogas stream consisting essentially of methane gas and into an exhaust gas stream containing undesired substances, said exhaust gas stream being thermally or catalytically oxidized. According to the invention, the exhaust gas stream is guided prior to oxidation through closed storage containers and/or fermentation residue containers for the inertization of explosive gas concentrations resulting there.

9 Claims, 3 Drawing Sheets

METHOD FOR BIOGAS TREATMENT AND BIOGAS INSTALLATION

CROSS-REFERENCE TO RELATED APPLICATIONS

Figure 1:
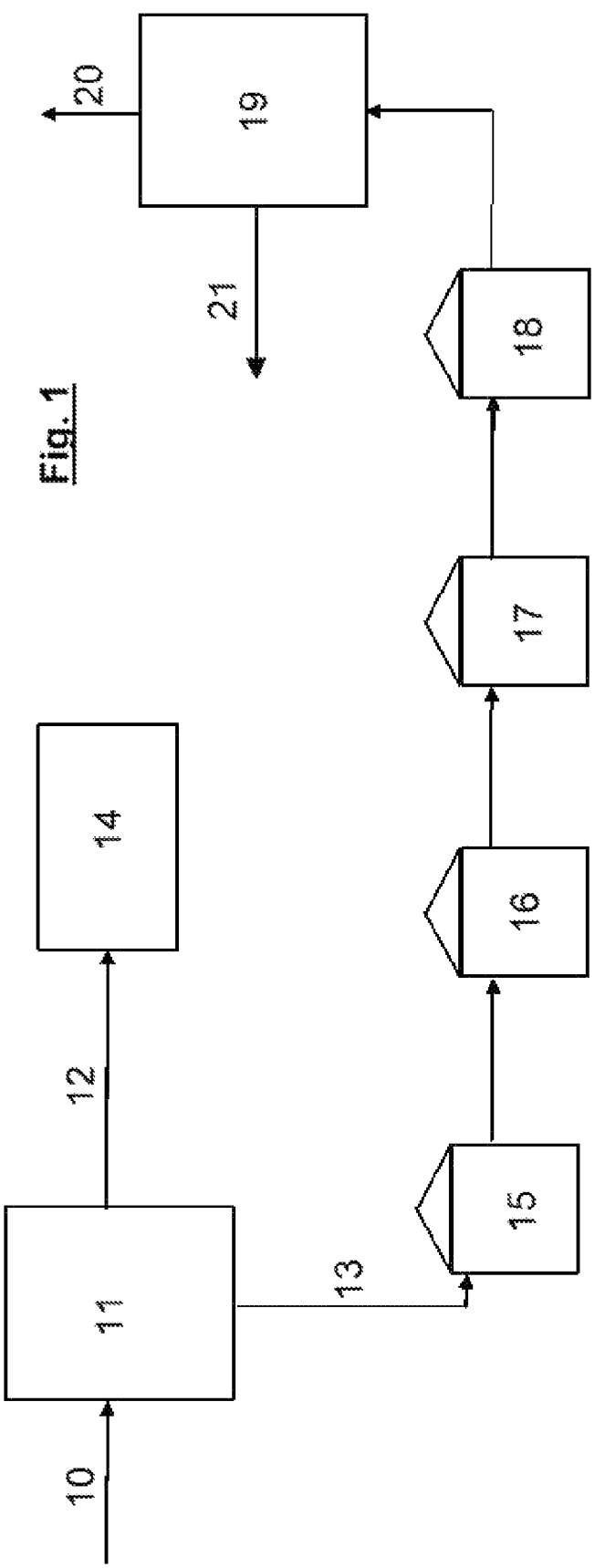

This application is a National Phase Application of PCT International Patent Application No. PCT/DE2009/075044, International Filing Date Aug. 24, 2009, which claims priority under 35 USC §119(e) of German Patent Application No. 10 2008 046 879.7, filed on Sep. 11, 2008, the contents of which are hereby incorporated by reference.

The invention relates to a method for biogas treatment in which the gas arising from a fermentation process is separated into a useable biogas stream consisting essentially of methane gas and into a waste gas stream that contains detrimental substances (essentially carbon dioxide) and that is thermally or catalytically oxidized.

The invention also relates to a biogas installation with one or more fermentation tanks and, if applicable, with post-fermentation tanks, with a biogas treatment plant for separating biogas from waste gas, whereby a waste-gas transport system has a final thermal or catalytic oxidation stage, as well as with at least one reservoir and/or fermentation residue storage tank.

The anaerobic fermentation of organic substances gives rise to, among other things, methane, which is a high-grade energy source whose energy content can be utilized, for instance, for heating purposes. Other gas components that are formed within the scope of a fermentation process include carbon dioxide, hydrogen sulfide, nitrogen and other detrimental substances. It is a known approach in the biogas treatment to segregate a gas stream consisting essentially of methane, which can then be fed directly into the gas pipeline network. In order to treat raw biogases arising from a fermentation process, it is necessary to carry out biogas desulfurization, gas drying and especially carbon dioxide separation. The carbon dioxide can be separated according to the state of the art, for example, by means of gas scrubbing employing a scrubbing liquid (e.g. water, polyglycol, MEA—monoethanol amine scrubbing), by means of pressure swing adsorption (PSA), by means of a membrane separation process (wet or dry) or by means of carbon dioxide liquefaction.

For environmental as well as economic reasons, there is a need to minimize the losses of methane during the treatment of the raw biogas. By the same token, emissions of methane or carbon dioxide into the atmosphere should be avoided in view of the greenhouse effect as set forth in the convention on climate change. For technical reasons, the carbon dioxide separation processes known from the state of the art entail a methane loss that, depending on the $CO_2$ separation method employed, fluctuates between 2 vol-% and 6 vol-% (since all of the gases that occur in the biogas installation are virtually "ideal gases", the specifications in vol-% can be equated with mole-%). This is why the waste gas stream has to undergo a waste gas treatment in almost all biogas treatment. Experts make a fundamental distinction between the methane loss—in other words, the amount of methane that cannot be fed into the gas network—and the methane concentration in the waste gas stream. For example, during the treatment of biogas with a methane content of 53 vol-% and a methane loss of 3 vol-% as well as with a methane content of 96 vol-% in the product gas to be fed in, the waste gas has a methane concentration of 3.42 vol-%. For purposes of minimizing the release of methane into the environment from biogas installations, legislators in Germany have instituted financial incentives (e.g. the "Technology Bonus" based on the German Renewable Energy Act (Erneuerbare-Energien-Gesetz—EEG) in which, however, the maximum permissible emission of methane in the waste gas from a biogas treatment process is limited to 0.5 vol-% of the methane mass produced in the biogas process. In order to reduce the methane concentration to the required value of 0.5 vol-% in the example given, in general, the waste gas is thermally or catalytically oxidized. Towards this end, it is a known practice to employ so-called FLOX burners, that is to say, burners with flameless oxidation, or catalytic after-burning. In order to carry out the after-burning, it can be necessary to admix biogas, natural gas or liquefied gas.

Moreover, it is likewise a well-known procedure according to the state of the art to treat the organic substances used for the fermentation or to place them into in-process storage prior to the fermentation. Consequently, it is quite common for solid substances either to be introduced directly into the fermentation stage or else to flow in via various systems, whereas liquid raw materials such as liquid manure or other pumpable organic wastes are usually buffered in one or more reservoirs. Recirculated products, in other words, substrates stemming from different areas of the installation and/or from a separation step, can be returned to such reservoirs before they are conveyed to one or more fermenters and subsequently to the post-fermentation tanks that are present. The fermentation residue is placed into in-process storage in so-called fermentation residue storage tanks or fermentation residue tanks or substrate storage tanks or final storage tanks so that they can undergo further treatment or can be spread onto agricultural farmland. Gases are formed in these reservoirs and in the fermentation residue storage tanks, and the type and composition of these gases are a function of the biological activity and the organic degree of biodegradation of the substances stored in the tanks. Whereas the formation of biogas in the fermenter or in the post-fermentation tanks is desired and is promoted by the conditions that are selected, the formation of gas in reservoirs and fermentation residue storage tanks has a detrimental effect. Admixing fresh, relatively dry organic substances such as, for example, silage with an active fermenter content, or introducing the liquid phase stemming from the solid-liquid separation of active fermenter material into the fermentation process of upstream and downstream tanks gives rise to detrimental gas formation.

According to the current state of the art, reservoirs and/or fermentation residue storage tanks are sometimes open, sometimes they are designed without a gas-tight cover, so that the gases that are formed escape freely into the atmosphere. The emitted gas mixtures contain not only malodorous gases such as, for instance, hydrogen sulfide, ammonia and mercaptans or alkane thiols, but especially also carbon dioxide and methane which, despite being odorless, are considered as to be the main culprits in anthropogenic global warming.

Methane is a greenhouse gas that is approximately 25 times more active than carbon dioxide and consequently, it is globally regarded as one of the gases responsible for the greenhouse effect. The oxidation of the methane to form carbon dioxide and water already reduces the greenhouse effect by a factor of 25. This is also the reason why new statutory regulations require a reduction in the percentage of methane gas in the emissions of biogas installations. Legal incentives for reducing the emission of methane are created in that subsidies that could otherwise be granted are not given as long as the biogas installation does not have tanks that are sealed gas-tight. A gas-tight covering on the fermentation residue storage tanks and the reservoirs, however, gives rise to new problems since, above a given concentration, the methane gases being formed are explosive at normal pressure if they come into contact with air at the ambient temperature, so that additional measures have to be implemented for explosion protection. The greatest risk arises when the fermentation residue storage tanks are emptied at the time when the fermentation residues are being removed, so that the space created by this emptying procedure can hold large volumes of explosive gases. The statutory requirements aimed at preventing explosions in biogas installations, however, mean that the explosion-protection measures make the generation of biogas altogether more expensive. In Germany, for example, the following regulations apply to a biogas installation:

"Vierte Verordnung zur Durchführung des Bundes-Immissionsschutzgesetzes (Verordnung über genehmigungsbedürftige Anlagen-4. BImSchV)" [Fourth directive on the implementation of the German Federal Emission Control Act (directive on installations that require a permit)];

"Zwölfte Verordnung zur Durchführung des Bundes-Immissionsschutzgesetzes (Störfall-Verordnung-12. BImSchV)" [Twelfth directive on the implementation of the German Federal Emission Control Act (industrial accident regulations)];

"Sicherheitsregeln für landwirtschaftliche Biogasanlagen", [Safety rules for agricultural biogas installations"], Safety distances pursuant to Point 2.4.5.4, balloon and cushion storage units as well as sheet storage over liquid manure storage tanks or fermentation tanks.

Comparable regulations exist in other countries.

The present invention is based on the objective of creating a method for biogas treatment as well as a biogas installation that provides sufficient protection against explosions and that is nevertheless set up in a simple manner, so as to allow optimal, cost-effective operation.

This objective is achieved by the method according to claim 1 as well as by the biogas installation according to claim 4. Refinements are described in the subordinate claims.

The core idea of the present invention is that, before the final oxidation procedure, the waste gas stream arising from the biogas treatment process is conveyed through the reservoirs and/or through the fermentation residue storage tanks, which have a closed design. Therefore, this waste gas stream—which consists essentially of carbon dioxide and only small amounts of methane—serves to inertize the gas volumes of the reservoirs and/or of the fermentation residue storage tanks. These free volumes are thus flooded with the waste gas stream, which prevents explosive gas mixtures from forming or concentrations that would cause explosions from being exceeded. This flushing effect can be handled without the use of extensive resources and avoids the need for capital expenditures to comply with explosion-protection measures that are otherwise prescribed by law.

The waste gas stream can flow through the existent reservoirs and/or fermentation residue storage tanks which are otherwise sealed gas-tight, preferably one after the other. This configuration has the advantage that a gas storage volume, which is needed to regulate the thermal or catalytic oxidation and whose filling level can be monitored, only has to be created in the last tank through which the waste gas stream flows.

Another advantage is that the gas spaces of all of the tanks are continuously flushed with the entire waste gas stream, so that no areas can form where the methane could reach high concentrations.

The present invention thus relates to a method for biogas treatment in which the biogas arising from a fermentation process is separated into a directly useable gas stream consisting essentially of methane gas, and into a waste gas stream that contains detrimental substances and that is thermally or catalytically oxidized. Before the oxidation procedure, the waste gas stream is conveyed through reservoirs and/or fermentation residue storage tanks, which have a closed design.

The term "gas stream consisting essentially of methane gas" as set forth within the scope of the present invention refers to a gas stream that contains at least 90 vol-%, preferably 95 vol-%, of methane.

The waste gas stream could, of course, also flow through the tanks in a parallel flow, making it necessary for the waste gas stream stemming from the biogas treatment to be divided in as many partial streams as there are tanks, so as to ensure an adequate gas feed to each reservoir and/or fermentation residue tank. The gas outlets of all of the tanks go to a shared waste gas line that leads to the thermal or catalytic oxidation stage.

Preferably, the waste gas is subsequently burned, and the combustion heat is utilized in order to meet the heat demand of the biogas installation and, if applicable, of external heat consumers.

In contrast to the methods known from the state of the art, the waste gas stream containing mainly $CO_2$ as well as small amounts of methane is not conveyed through the fermentation tanks, post-fermentation tanks or bioreactors that serve to generate biogas, but rather, only through the gas-tight covered tanks of a biogas installation such as the reservoirs and/or the fermentation residue tanks, where the production of methane and of gas containing $CO_2$ is basically undesired since this gives rise to problems with environmentally harmful emissions and occupational safety. The gas stream containing mainly $CO_2$ as well as small amounts of methane is not fed into liquid phases that have a solid fraction and that contain the substrate, but rather, it is only conveyed through other gaseous phases so that the concentrations of the gas mixtures present there are changed in the manner according to the invention. Even though the inventive treatment of the waste gas stream does not serve to increase the methane yield in the biogas generated by the fermentation process, a positive effect is exerted on the energy balance of the entire installation since in that the methane contained in the waste gas stream as well as the methane formed in the reservoirs and/or in the fermentation residue storage tanks can be converted into thermal energy by means of a downstream oxidation procedure, and this energy can likewise be utilized (for instance, in order to meet the heat demand of the biogas installation itself).

The inventive minimization of the mass of combustible and highly flammable gases in the reservoirs and in the fermentation residue storage tanks reduces the need for extensive explosion-protection measures.

As a rule, the waste gas stream of biogas treatment plants contains 2.3 vol-% to 6.4 vol-% of methane and 96.7 vol-% to 93.6 vol-% of carbon dioxide. The remainder is made up of small percentages of nitrogen, oxygen, hydrogen and hydrogen sulfide. Methane gas mixtures can be explosive at normal pressure at 20° C. [68° F.] with a methane content of 4.3 vol-% as the lower explosion limit and 16.3 vol-% as the upper explosion limit (at 100° C. [212° F.], the lower limit is 4.0% and the upper limit is 17.3%), however, this is only the case if the percentage of inert gas (e.g. $CO_2$) is below 30.5 vol-% (at 100° C. [212° F.] with an inert gas content of at least 33.5 vol-%). Further information on the explosion ranges of methane gas mixtures are known to the person skilled in the art from diagrams in triangular coordinates. Consequently, the waste gas of the biogas treatment plant with its high inert gas content of more than 90 vol-% is not explosive and can be utilized to inertize the free spaces in the reservoirs and in the fermentation residue storage tanks. The air present is displaced by means of the waste gas stream that serves to inertize the free spaces in the reservoir and in the fermentation residue storage tanks already before the individual tanks are filled with fermentation substrate or with fermentation residues. During the operation of the installation, the continuous inertization of the gas areas in the reservoirs and in the fermentation residue storage tanks serves to dilute the small amounts of biogas having a high content of methane that are formed there, and also to obtain a high content of inert gas ($CO_2$ here), so that explosion protection can be ensured. The concentration consistently remains below the limit value of 17.5 vol-% of methane at which a methane gas mixture at normal pressure is flammable at ambient temperature once it has come into contact with air and has thus been diluted.

Moreover, the configuration of the tanks, which are closed, except for the inlet and outlet of the waste gas stream, also prevents odors from being released as well as methane and/or carbon dioxide from being emitted. The waste gas stream, which has flowed either in parallel or in series through the reservoirs and the fermentation residue storage tanks, is subsequently oxidized, especially burned. Here, the methane formed in the tank as well as the methane slip of the gas treatment serve as fuel. The surplus thermal output of the exothermal reaction during the waste gas treatment is diverted into a heating system and can be employed, for instance, to meet the heat demand of the biogas installation and, if applicable, other heat consumers. Here, on the basis of method according to the invention, not only the energy content of the methane fraction stemming from the waste gas stream—in other words, basically the methane loss during the biogas treatment—but also the energy content of the methane fraction stemming from the additional, relatively small, biogas production in the reservoirs and in the fermentation residue storage tanks can be used. The utilization of these methane fractions makes sense from a cost standpoint, since the inventive utilization of the waste gas stream can be implemented technically without a great deal of investment.

Figure 2:
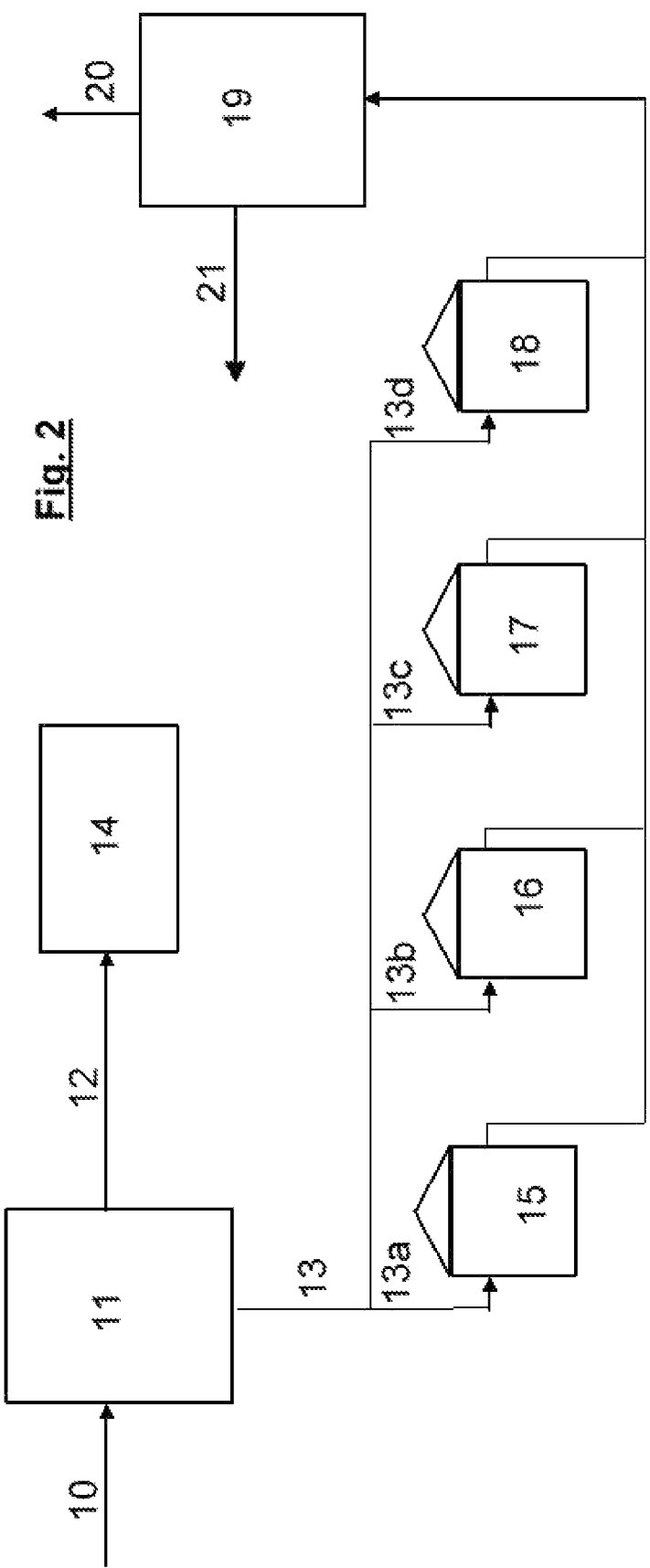
Figure 3:
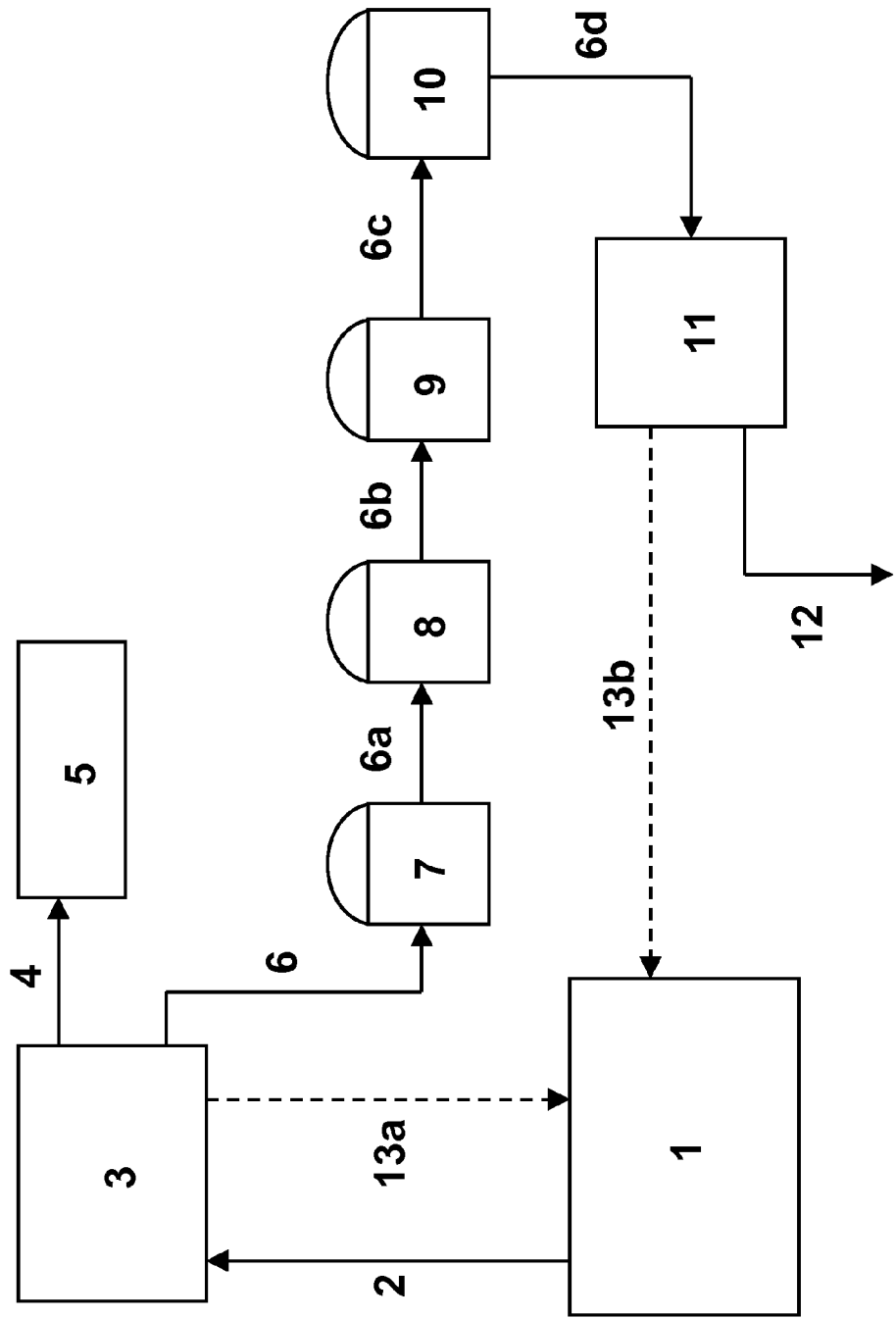

Embodiments of the present invention are elucidated in the drawings as well as in additional examples of the technical execution. The following is shown:

FIGS. 1 and 2: in each case, a schematic diagram of the biogas and waste gas transport system; and FIG. 3: a diagram of a 6.5 MW biogas installation according to the invention.

As shown in FIG. 1, the biogas stemming from the fermentation process 10 is conveyed to a biogas treatment plant 11 that separates the product gas stream 12 consisting essentially of methane gas from the waste gas stream 13 containing essentially $CO_2$. The product gas stream can be fed into the gas pipeline network 14. In accordance with the arrangement shown in FIG. 1, the product gas stream is conveyed consecutively into a reservoir 15 as well as into fermentation residue storage tanks 16, 17 and 18, through each of which the waste gas stream flows before it is fed to a thermal or catalytic oxidation stage 19 (serial arrangement). The arrangement shown in FIG. 2 differs from the previously described arrangement in that the waste gas stream 13 is divided into several partial streams 13a, 13b, 13c and 13d, each of which is fed separately into the tanks 15 to 18 (parallel arrangement). In addition to a gas inlet line, these tanks also have a gas outlet line, whereby the gas outlet lines coming from the various tanks 15, 16, 17 and 18 open up into a shared line that leads to the thermal or catalytic oxidation stage 19. The waste gases 20 obtained from the thermal or catalytic oxidation stage can be released into the atmosphere or can be conveyed to another treatment or utilization. The heat 21 generated during the thermal or catalytic oxidation stage can be employed to meet the heat demand of the biogas installation and optionally of external heat consumers.

Irrespective of whether an installation according to FIG. 1 or 2 is selected, the amount of combustible and highly flammable gases that are generated in the reservoirs and fermentation residue storage tanks can be advantageously reduced to a content that is no longer explosive. The closed configuration of all of the tanks 15 to 18 avoids diffuse gas emissions. The emission of methane is prevented by the post-oxidation. The entire installation and the process control are structured in a simple manner and meet the statutory stipulations.

The embodiment depicted in FIG. 3 shows the actual technical implementation of a 6.5 MW biogas installation that operates with a serial flow of the waste gas streams on the basis of the method according to the invention as shown in FIG. 1.

The biogas produced in the biogas fermenter 1 flows through the gas line 2 (volumetric flow rate of 1,200 $m^3/h$, methane content of 53%) to the biogas treatment plant 3. Following the biogas treatment (desulfurization, carbon dioxide separation via pressure swing adsorption—PSA), a product gas stream (volumetric flow rate of 643 $m^3/h$, methane content of 96%) flows through the pipeline 4 to the product gas feed unit 5. The waste gas stream consisting mainly of the inert gas $CO_2$, is conveyed consecutively via the pipeline 6 (volumetric flow rate of 572 $m^3/h$, methane content of 3.3%) through the gas-tight fermentation residue storage tanks 7, 8 and 9, and subsequently through the gas-tight reservoir 10 for inertization purposes. The waste gas streams 6a (volumetric flow rate of 580 $m^3/h$) and 6b (volumetric flow rate of 588 $m^3/h$) are formed between the fermentation residue storage tanks 7, 8 and 9, and the waste gas stream 6c (volumetric flow rate of 596 $m^3/h$, methane content of 5.3%) is formed between the last fermentation residue storage tank 9 and the reservoir 10, while the waste gas stream 6d (volumetric flow rate of 601 $m^3/h$, methane content of 5.8%) is formed downstream from the reservoir 10. The waste gas stream 6d flows through a pipeline into the FLOX burner and boiler system 11, where the flameless oxidation takes place. From the FLOX burner and boiler system 11, the residual waste gas is discharged into the environment through the line 12. Heat is generated in the biogas treatment plant 3 as well as in the FLOX burner and boiler system 11, and this heat is once again fed to the biogas installation via the routes 13a and 13b. In this process, a heat storage unit is charged via heat exchangers, and the heat for the biogas installation is obtained from said heat storage unit. Here, the transfer medium is usually water or a water-glycol mixture.

The characteristic values compiled in Table 1 were determined for the individual gas streams of the biogas installation described in FIG. 3.

TABLE 1

Characteristic values for the gas streams of the described 6.5 MW biogas installation.

| Biogas: | |
|---|---|
| volumetric flow rate | 1,200 $m^3/h$ |
| methane content | 53 vol-% |
| methane volumetric flow rate | 636 $m^3/h$ |
| Internal desulfurization: | |
| air volumetric flow rate | 15 $m^3/h$ |
| oxygen volumetric flow rate of the biogas | 3.15 $m^3/h$ |
| nitrogen volumetric flow rate of the biogas | 11.85 $m^3/h$ |
| oxygen content in the biogas | 0.26 vol-% |
| nitrogen content in the biogas | 0.98 vol-% |

TABLE 1-continued

Characteristic values for the gas streams of the described 6.5 MW biogas installation.

| | |
|---|---|
| total biogas/air volumetric flow rate | 1,215 m³/h |
| Raw biogas after desulfurization: | |
| volumetric flow rate | 1,215 m³/h |
| methane content | 52.3 vol-% |
| Biogas treatment (pressure swing adsorption - PSA): | |
| methane slip | 3.0 vol-% |
| Volumetric flow rate of the product gas | 643 m³/h |
| methane content of the product gas | 96.0 vol-% |
| separated fraction of oxygen | 50.0% |
| separated fraction of nitrogen | 50.0% |
| oxygen volumetric flow rate of the product gas | 1.58 m³/h |
| nitrogen volumetric flow rate of the product gas | 5.93 m³/h |
| oxygen content in the product gas | 0.25 vol-% |
| nitrogen content in the product gas | 0.92 vol-% |
| Volumetric flow rate of the waste gas | 572 m³/h |
| volumetric flow rate of methane in the waste gas | 19.1 m³/h |
| oxygen volumetric flow rate of the waste gas | 1.58 m³/h |
| nitrogen volumetric flow rate of the waste gas | 5.93 m³/h |
| oxygen content in the waste gas | 0.28 vol-% |
| nitrogen content in the waste gas | 1.04 vol-% |
| methane content in the waste gas | 3.33 vol-% |
| Fermentation residue storage tank as buffer for the waste gas from the PSA: | |
| biogas formation | 2.0% of above-mentioned biogas production |
| biogas formation | 24.0 m³/h |
| maximum $H_2S$ content in the biogas formed | 300.00 ppm |
| methane formation | 12.7 m³/h |
| methane input via the waste gas from the PSA | 19.1 m³/h |
| methane fraction | 5.33 vol-% |
| required operating gas storage volume | 1,622 m³ |
| Reservoir as buffer for the waste gas from the PSA: | |
| biogas formation | 5.0 m³/h |
| maximum $H_2S$ content in the biogas formed | 300.00 ppm |
| methane formation | 2.7 m³/h |
| methane input from the fermentation residue storage tank | 43/1 m³/h |
| total methane fraction | 5.84 vol-% |
| Waste gas from the storage tank for the waste gas treatment: | |
| volumetric flow rate | 601 m³/h |
| $H_2S$ content | 14.47 ppm |
| total methane fraction | 5.84 vol-% |
| oxygen content in the waste gas | 0.26 vol-% |
| nitrogen content in the waste gas | 0.99 vol-% |
| minimum temperature | 5° C. [41° F.] |
| maximum temperature | 60° C. [140° F.] |
| maximum moisture content | 100% |

The volumetric flow rates for the waste gas used for the inertization were calculated on the basis of the information in Table 2. The components of the biogas installation were numbered analogously to FIG. 3.

TABLE 2

Waste gas streams that were used for the inertization of the fermentation residue storage tanks and the reservoirs.

| | |
|---|---|
| Pipeline from PSA 3 to fermentation residue storage tank 7 | |
| volumetric flow rate | 572 m³/h |
| dimension | DN 150 |
| inner diameter | 152.2 mm |
| flow rate | 8.74 m/s |
| pressure loss | 7.3 mbar |
| Pipeline from fermentation residue storage tank 7 | |

TABLE 2-continued

Waste gas streams that were used for the inertization of the fermentation residue storage tanks and the reservoirs.

| | |
|---|---|
| to fermentation residue storage tank 8 | |
| volumetric flow rate$_{[n1]}$ | 580 m³/h |
| dimension | DN 300 |
| inner diameter | 302.6 mm |
| flow rate | 4.41 m/s |
| pressure loss | 0.3 bar |
| Pipeline from fermentation residue storage tank 8 to fermentation residue storage tank 9 | |
| volumetric flow rate$_{[n2]}$ | 588 m³/h |
| dimension | DN 300 |
| inner diameter | 302.6 mm |
| flow rate | 6.61 m/s |
| pressure loss | 0.7 bar |
| Pipeline from fermentation residue storage tank 9 to reservoir 10 | |
| volumetric flow rate$_{[n3]}$ | 596 m³/h |
| dimension | DN 300 |
| inner diameter | 302.6 mm |
| flow rate | 2.51 m/s |
| pressure loss | 0.15 bar |
| Pipeline from reservoir 10 to FLOX burner 11 | |
| volumetric flow rate$_{[n4]}$ | 601 m³/h |
| dimension | DN 200 |
| inner diameter | 206.5 mm |
| flow rate | 5.39 m/s |
| pressure loss | 1.25 bar |

Concerning the mass balance of the generated gases from the entire installation, gas quantities as compiled in Table 3, with the corresponding proportional compositions of the gases methane, oxygen, nitrogen, hydrogen sulfide and carbon dioxide are yielded. In this context, it was assumed that the installation was in operation 365 days per year, 24 hours per day.

TABLE 3

Gas mass balance and gas composition for the 6.5 MW biogas installation as shown in FIG. 3.

| Gas | Amount [m³/yr] | $CH_4$ [%] | $O_2$ [%] | $N_2$ [%] | $H_2S$ [ppm] | $CO_2$ [%] |
|---|---|---|---|---|---|---|
| raw biogas | 10,643,400 | 52.3 | 0.26 | 0.98 | <300 | 46.42 |
| product gas | 5,629,395 | 96.0 | 0.25 | 0.92 | 0 | 2.83 |
| inert gas | 5,014,005 | 3.3 | 0.28 | 1.04 | 0 | 95.36 |
| gas formation in fermentation residue storage tank | 210,240 | 53 | 0 | 0 | <300 | 47.00 |
| gas formation in reservoir | 43,800 | 53 | 0 | 0 | <300 | 47.00 |
| gas utilization in the FLOX burner | 5,268,045 | 5.84 | 0.26 | 0.99 | 14.47 | 92.91 |

It has been found that, in a biogas installation configured according to the invention, the method according to the invention—in which, before the final oxidation procedure, the waste gas stream stemming from the biogas treatment is conveyed through the fermentation residue tanks and the reservoirs, which have a closed design—is suitable to ensure explosion protection as well as to utilize the energy of the biogas that is additionally formed in the fermentation residue storage tanks and in the reservoirs. The waste gas from the biogas treatment had a concentration of methane of 3.3 vol-% and of carbon dioxide of 95.4 vol-%, so that, owing to its composition, it was very well suited as a gas for the inertization of fermentation residue tanks and reservoirs. The volume of the resultant waste gas streams was completely sufficient to inertize the biogas generated in the fermentation residue tanks and in the reservoir, so that the methane content was 5.33 vol-% after the waste gas streams had flowed in series through the three fermentation residue storage tanks, and then 5.84 vol-% after having additionally flowed through the reservoir. Therefore, in any case, the methane concentration in the free gas volumes inside the reservoirs and the fermentation residue tanks was well below the limit of 17.5%, above which an explosive mixture could arise in the case of contact with air. The risk of explosion inside the closed reservoirs and fermentation residue tanks is already eliminated by the high $CO_2$ fraction, which functions as an inert gas. The biogas formed in the fermentation residue tanks and in the reservoir, at a volume of 254,040 $m^3$/yr, accounts for 2.4% of the biogas formed in the fermenter, and, thanks to the subsequent oxidation in the FLOX burner, it could also be utilized as thermal energy to heat the biogas fermenter. The closed configuration of the fermentation residue tanks and of the reservoir as well as the flameless oxidation of the residual waste gas prevented the emission of methane and carbon dioxide into the environment, so that climate-change aspects have also been taken into consideration in the method according to the invention and in the biogas installation according to the invention.

The invention claimed is:

1. A method for biogas treatment in which the biogas arising from a fermentation process is separated into a directly useable gas stream consisting essentially of methane gas and into a waste gas stream that contains detrimental substances and that is thermally or catalytically oxidized, characterized in that, before an oxidation procedure, the waste gas stream is conveyed through reservoirs and/or fermentation residue storage tanks, which have a closed design, wherein the waste gas stream inertizes the gas volumes of the reservoirs and/or the fermentation residue storage tanks.

2. The method according to claim 1, characterized in that the waste gas flows through the reservoirs and/or through the fermentation residue storage tanks one after the other, or it is divided into several partial subsets, each of which is fed separately into the reservoirs and/or into the fermentation residue storage tanks.

3. The method according to claim 1, characterized in that the waste gas is subsequently burned, and the combustion heat is utilized in order to meet the heat demand of the biogas installation.

4. The method of claim 3 wherein the combustion heat is utilized to meet the heat demand of external heat customers.

5. The method of claim 1 wherein fermentation substrates are used either as intermediate stores for subsequent entry of the fermentation substrates into fermenters or as stores for fermentation residue produced after the fermentation process.

6. A method for biogas treatment comprising the steps of:
separating the biogas arising from a fermentation process is separated into a directly useable gas stream consisting essentially of methane gas and into a waste gas stream that contains detrimental substances;
conveying the waste gas stream through closed design reservoirs and/or closed design fermentation residue storage tanks;
continuously flushing the entire waste gas stream, wherein the concentration of methane remains below about 17.5% by volume;
inertizing the gas volumes of the reservoirs and/or tanks with the waste gas stream; and,
thermally or catalytically oxidizing the waste gas stream.

7. The method of claim 6, wherein the method further comprises the steps of:
diverting the surplus thermal output of an exothermal reaction during the waste gas treatment into a heating system.

8. The method of claim 6, wherein the waste gas stream flows through multiple residue storage tanks arranged in serial formation.

9. The method of claim 6, wherein the waste gas stream is divided into multiple partial streams, which are each fed separately into storage tanks arranged in parallel formation.

* * * * *